United States Patent [19]

Bell

[11] Patent Number: 4,904,695

[45] Date of Patent: Feb. 27, 1990

[54] INSECTICIDAL AQUEOUS-BASED MICROEMULSION COMPOSITIONS

[75] Inventor: Mark Bell, Hampshire, England

[73] Assignee: American Cyanamid Company, Stamford, Conn.

[21] Appl. No.: 892,972

[22] Filed: Aug. 4, 1986

Related U.S. Application Data

[63] Continuation of Ser. No. 598,140, Apr. 9, 1984, abandoned.

[51] Int. Cl.$^4$ ............................................. A01N 37/34
[52] U.S. Cl. ..................................................... 514/521
[58] Field of Search ......................................... 514/521

[56] References Cited

U.S. PATENT DOCUMENTS 4,283,415  8/1981  Fuyama et al. ..................... 514/521
4,459,150  7/1984  Hatton et al. ............................ 71/92

OTHER PUBLICATIONS

Chemical Abstracts, vol.96 (1982); #195083s; Roberts. Rhone-Poulenc; "Soprosole"; Mar. 1981.

*Primary Examiner*—Joseph A. Lipovsky
*Attorney, Agent, or Firm*—John W. Hogan, Jr.

[57] ABSTRACT

The present invention relates to novel insecticidal aqueous-based microemulsion compositions and methods for controlling insects with said aqueous-based microemulsions. The microemulsions of the present invention contain a synthetic pyrethroid or organophosphate insecticide, a certain surfactant blend, microemulsion adjuvants such as antifoamers, antifreezing agents, thickeners and preservatives and provide thermodynamically, stable compositions uniquely suited for ultra-low volume (ULV) applications in combatting insect pests.

17 Claims, No Drawings

INSECTICIDAL AQUEOUS-BASED MICROEMULSION COMPOSITIONS

This is a continuation of application Ser. No. 598,140, filed Apr. 9, 1984, now abandoned.

BACKGROUND OF THE INVENTION

The present invention relates to novel pesticidal aqueous-based microemulsions and methods for using said microemulsions for controlling insect pests.

Aqueous pesticidal formulations have attracted considerable interest in recent years because such formulations possess certain advantages over non-aqueous systems. One such advantage such suspension concentrates, concentrated emulsions, and flowable possess includes the reduction or elimination in using organic solvents. This reduction or elimination of organic solvent use then results in reduced phytotoxicity (encouraged by some organic solvents); decreases in costs when compared to organic-based systems; safer handling; compatibility with a greater variety of packaging materials; and, in some instances, enhanced biological activity.

Recently, concentrated aqueous emulsions have been introduced as alternative pesticidal formulations to emulsifiable concentrates. The successful introduction of such emulsion compositions is due to advances made both in understanding formulating such emulsions and understanding factors influencing emulsion stability. Even with such advances in understanding emulsion stability, it is known that the high surface area created in preparations of this sort is usually accompanied by large surface free energies. This, in turn, creates the opportunity for a variety of breakdown processes, and therefore, while the kinetic stability of these emulsions (dispersions) may be increased, they still represent thermodynamically-unstable systems.

Microemulsions, on the other hand, present a unique class of thermodynamically-stable liquid dispersions. This stability is attributed to the presence of near zero interfacial tensions at equilibrium and also a minimum or potentially negative Gibbs free-energy term for the system. In order to achieve low interfacial tensions, the use of several surfactants is usually required. When one of the surfactants is soluble in the water phase and the other is soluble in the organic phase, each one has only a marginal effect on the other, and their combined effect may be large enough to reduce the interfacial tension to near zero at finite concentrations. Thus, although microemulsions are obtainable with certain surfactant combinations and within finite concentrations of these surfactant combinations, at present, formulating such microemulsions is still an art.

SUMMARY OF THE INVENTION

The present invention, therefore, relates to novel insecticidal microemulsion compositions which are aqueous based. These microemulsions are comprised of about 1% to 20%, on a weight to volume basis, of an insecticide and about 1.0% to 40%, preferably 1.25% to 40%, on a weight to volume basis, of a certain surfactant blend plus water. These microemulsions can also contain microemulsion adjuvants such as antifoaming agents, antifreezing agents, viscosity-adjusting agents (thickening agents), and antimicrobial preservatives, with the remainder being water.

These aqueous-based insecticidal microemulions are thermodynamically stable and exhibit exceptional stability over a wide range of temperatures.

Furthermore, it is an additional object of the present invention to provide such temperature-stable microemulsions in a clear to opaque form.

Additionally, another object of this invention is to provide methods whereby such microemulsions are useful in combatting insect pests, especially methods wherein the microemulsions of the invention are applied utilizing ultra-low volume (ULV) applications. These and other objects will become apparent by the more detailed description of the invention that follows.

DESCRIPTION OF THE INVENTION

The present invention is a novel, aqueous-based insecticidal microemulsion composition comprising about 1% to 20%, on a weight to volume basis, of an insecticide, such as the synthetic pyrethroid, $(\pm)$-$\alpha$-cyano-m-phenoxybenzyl $(+)$-2-[(p-difluoromethoxy)-phenyl]-3-methylbutyrate, among others; about 1.25% to 40%, on a weight to volume basis, of a surfactant blend such as calcium dodecylbenzene sulfonate, ethoxylated distyrylphenol ammonium sulfate with 5 moles of ethoxylation, and/or ethoxylated tristyrylphenol with 17 moles of ethoxylation; and optionally, about 0.0% to 1.0%, on a weight to volume basis, of an antifoaming agent, such as a silicone emulsion; with up to about (0% to 10%) 10%, on a weight to volume basis, of an antifreezing agent, such as alkyldiol or dialkyldiol, if needed; plus water added to bring the composition to 100%. Additionally, it has been found that the viscosity of the thus-formed microemulsions may be modified by the addition of thickening agents, such as cellulose derivatives, polyacrylamides, polyvinyl alcohols, polyvinyl pyrollidones, natural gums, and the like, as required. Suitable preservatives useful in the present invention include methylparaben at levels of about 0.0% to 0.2%.

Preferred surfactant blends of the present novel insecticidal microemulsion compositions include mixtures of a 70% alcoholic solution of calcium dodecylbenzene sulfonate with ethoxylated distyrylphenol ammonium sulfate (5 moles ethoxylation) and/or ethoxylated tristyrylphenol (17 moles ethoxylation). The preferred ratios of such surfactants in combinations are 3:7:5; 1:14:0; and 6:0:9, respectively.

The insecticidal microemulsion compositions of the invention may conveniently be prepared by admixing from 1% to 20% of an insecticide, on a weight to volume basis, such as the synthetic pyrethroid $(\pm)$-$\alpha$-cyano-m-phenoxybenzyl alcohol ester of $(+)$-2-[(p-difluoromethoxy)phenyl]-3-methylbutyrate, with about 1.25% to 40%, on a weight to volume basis, of an appropriate surfactant mixture in water containing about 0% to 1.0% of an antifoaming agent. This is mixed until this resultant mixture clears and is homogeneous. Additional components, such as 0% to 10%, on a weight to volume basis, of antifreezing agents as well as any thickeners may then be admixed. This is followed by dilution with water to total the composition to 100%.

Alternatively, such compositions may be prepared by admixing the required amount of water to a mixture of surfactants combined with the synthetic pyrethroid or organophosphate. Then, the remaining ingredients may be added to the mixture.

It also has been found that the stability of such prepared aqueous-based insecticidal microemulsions may be enhanced by partial neutralization of acidic functions contained within the surfactants.

Furthermore, the aqueous-based microemulsion insecticidal compositions of the present invention contain finely-divided discreet droplets with a droplet mass median size of about 17μ to 150μ. This, in combination with the unique surface tensions, viscosity and evaporation rates of such microemulsions, makes such microemulsions extremely attractive and effective when used in ultra-low volume (ULV) applications.

Additionally, the resultant insecticidal microemulsion compositions of the present invention possess an additional advantage in that they have unexpectedly low volatilities in ranges of 20%–25% of that of water, when tested in a Piche evaporimeter. This allows for the selection of certain compositions, especially those containing about 0.1% to 1% thickeners, useful for direct application by ultra-low volume (ULV) techniques. Thus, the compositions of this invention allow for the direct application, utilizing ULV techniques, of water-based formulations of insecticides, such as synthetic pyrethroids and organophosphates in addition to the suitability of such microemulsions for use under a wide variety of climatic conditions.

It has been found that applying about 0.0025% to 1.5% of the active ingredient of the present, aqueous-based microemulsion to the habitat, food supply or breeding sites of insect pests, will produce effective control of such pests.

The compositions and methods of the present invention are further illustrated by the following non-limiting examples.

EXAMPLE 1

Preparation of Insecticidal Microemulsion Composition Containing Synthetic Pyrethroid A synthetic pyrethroid, at about 1.33% to 20.0%, on a weight to volume basis, is added to a stirred mixture containing about 0% to 1%, on a weight to volume basis, of a silicone antifoaming agent, the desired mixture of surfactants, as described in Table I, and 60% to 75% of the required water for higher pyrethroid concentrations or about 5% to 20% water for lower pyrethroid concentrations. After stirring to ensure the microemulsion formation, usually one-quarter to one hour, an antifreezing agent, such as ethylene glycol or diethylene glycol, at levels of about 0% to 10%, on a weight to volume basis, is added, and the microemulsion is diluted to 100% with water.

Thickening agents such as cellulose derivatives (and required preservatives), polyacrylamides, natural gums, polyvinyl alcohols, or pyrollidones, among others, may then be admixed, as required, to yield the insecticidal microemulsion compositions of Examples 1–12 presented in Table II.

TABLE I

| No. | Surfactant |
|---|---|
| A | Distyrylphenol ethoxylate ammonium sulfate (5 mols of ethoxylation) |
| B | Tristyrylphenol ethoxylate (17 mols of ethoxylation) |
| C | 70% alcoholic solution of calcium dodecylbenzene sulfonate |

TABLE II

| Example | Synthetic Pyrethroid % W/V | Surfactant % W/V A | B | C | Antifreeze % W/V | Antifoam % W/V | Additive % W/V |
|---|---|---|---|---|---|---|---|
| 1 | 1.33 | 1.33 | 0.889 | 0.533 | 2.0 | 0.05 | — |
| 2 | 1.33 | 1.33 | 0.889 | 0.533 | 2.0 | 0.05 | Sodium carboxy-oils |
| 3 | 1.33 | 1.33 | 0.889 | 0.533 | 2.0 | 0.05 | Polyacrylamide 0.375 |
| 4 | 1.33 | 0 | 1.60 | 1.07 | 2.0 | 0.05 | |
| 5 | 2.5 | 0 | 3.0 | 2.0 | 2.0 | 0.05 | |
| 6 | 2.5 | 0 | 3.0 | 2.0 | 2.0 | 0.05 | Polyacrylamide 0.375 |
| 7 | 4.0 | 3.75 | 2.67 | 1.6 | 2.0 | 0.05 | |
| 8 | 4.0 | 3.75 | 2.67 | 1.6 | 2.0 | 0.05 | Polyacrylamide 0.375 |
| 9 | 5.0 | 3.75 | 2.67 | 1.6 | 5.0 | 0.075 | — |
| 10 | 10.0 | 7.0 | 5.0 | 3.0 | 5.0 | 0.075 | |
| 11 | 10.0 | 14.0 | 0 | 1.0 | 0 | 0.075 | |
| 12 | 10.0 | 0 | 9.0 | 6.0 | 0 | 0.075 | |
| 13 | 20.0 | 0 | 15.0 | 10.0 | 0 | 0 | |

EXAMPLE 13

Insecticidal Activity of Insecticidal Microemulsion Compositions of the Invention Insecticidal aqueous microemulsion compositions containing 10%, on a weight to volume basis, of the synthetic pyrethroid, (±)-α-cyano-m-phenoxybenzyl (+0-2-[(p-difluoromethoxy)phenyl]-3-methylbutyrate, were tested for effectiveness in controlling insect pests under a variety of conditions. The results are tabulated in Table III.

TABLE III

| | INSECTICIDAL EFFECTIVENESS | | | |
|---|---|---|---|---|
| DOSAGE* | CROP | PEST | % CONTROL | COUNTRY |
| 0.0025% a.i. | Beans | *Tetranychus urticae* | 90 | U.S.A. |
| 0.005% a.i. | Beans | *Tetranychus urticae* | 93 | U.S.A. |
| 0.005% a.i. | Grape | *Lobesia botrana* | 97 | Italy |
| 0.004% a.i. | Artichoke | *Hydroecia* | | |

TABLE III-continued

| INSECTICIDAL EFFECTIVENESS | | | | |
|---|---|---|---|---|
| DOSAGE* | CROP | PEST | % CONTROL | COUNTRY |
| 30 g a.i./ha | Cotton | xanthenes<br>Heliothis | 97 | Spain |
|  |  | armigera | 97 | South Africa |
|  |  | Tetranychus<br>spp. | 97 | South Africa |
| 50 g a.i./ha | Cotton | Spodoptera<br>littoralis | 44 | Egypt |
| Lab. LO$_{50}$<br>Determination | Caster<br>Bean | Tetranychus<br>spp. | 14.2 ppm | Egypt |

*Spodoptera* = Cotton Leafworm
*Tetranychus* = Mites
*Lobesia botrana* = Grape Moth
*Heliothis armigera* = American Bollworm
*Hydroecia xanthenes* = Artichoke Borer
*a.i./h.a.

As is evident in reviewing TABLE III, the microemulsions of the present invention provide effective insecticidal activity for a variety of crops and under a variety of environmental conditions.

EXAMPLE 14

Preparation of Insecticidal Microemulsion for ULV (Ultra Low Volume) Application A solution of sodium carboxymethyl cellulose (0.5%, 1.5 kg) in water (300 liters), containing ethanediol and methylparaben (0.3 kg) was added to a 10% microemulsion prepared with the insecticide, (±)-α-cyano-m-phenylbenzyl (+)-2-[(p-difluoromethoxy)phenyl]-3-methylbutyrate (13.46 kg), the surfactants, ethoxylated (17-mols ethoxylation) tristyrylphenol (16.0 kg), a 70% alcoholic solution of calcium dodecylbenzenesulfonate (10.7-kg), and 401.6 liters of water; said solution also containing a silicone emulsion (0.5 kg), methylparaben (0.2 kg), and sufficient additional ethanediol to give 2.0 kg total in the final composition. The resulting mixture was stirred thoroughly, and this solution was then diluted with water to 1000.0 liters in order to result in an insecticidal microemulsion composition suitable for ULV application. This composition possesses the following properties:

Density, 1.00 g/mL @ 20° C.;

Surface tension, 0.0315 N/m @ 20° C. (du Noay method);

Evaporation rate, 0.042 mL/cm$^2$/24 hours;

(Water evaporation rate, 0.306 mL/cm$^2$/24 hours)

(Piche evaporimeter, 68% rh, 18° C. air current 0.1 m/s);

Viscosity, 8.6 cP @ 20° C. (Brookfield, #1 LV spindle, at 60 rpm).

Examples prepared as above possess evaporation rates, surface tensions and viscosities making them highly suitable for ULV application.

What is claimed is:

1. An aqueous-based insecticidal microemulsion composition comprising, on a weight to volume basis: about 1% to 20% of (±)-α-cyano-m-phenoxybenzyl (+)-2-[p-(difluoromethoxy)-phenyl]-3-methylbutyrate; about 1.0% to 40% of the surfactant blend consisting of one or more components selected from the group consisting of calcium dodecylbenzene sulfonate, ethoxylated distyrylphenol ammonium sulfate with 5 moles of ethoxylation and ethoxylated tristyrylphenol with 17 moles of ethoxylation; about 0% to 12% thickening agents, antifoaming agents, antifreezing agents, antimicrobial preservatives or mixtures thereof; and water to total said composition to 100%.

2. A composition according to claim 1, wherein said composition contains about 0% to 1.0% of an antifoaming agent; about 0% to 10% of an antifreezing agent; about 0.1% to 1.0% a thickening agent; and about 0.0% to 0.2% of an antimicrobial preservative.

3. A composition according to claim 2, wherein said surfactant blend is 1.25% to 40%, on a weight to volume basis, of said composition.

4. A composition according to claim 3, wherein said surfactant blend is a 70% alcoholic solution of calcium dodecylbenzene sulfonate, ethoxylated distyrylphenol ammonium sulfate with 5 moles of ethoxylation and ethoxylated tristyrylphenol with 17 moles of ethoxylation.

5. A composition according to claim 4, wherein said antifoaming agent is a silicone emulsion; said antifreezing agent is alkyl or dialkyl glycol; and said antimicrobial preservative is methylparaben.

6. A composition according to claim 5, wherein said thickening agent is a cellulose derivative polyacrylamides, polyvinyl alcohols, polyvinyl pyrollidones, natural gums or mixtures thereof.

7. A composition according to claim 6, wherein said composition comprises: about 5.0% ethylene glycol as said alkyl glycol antifreezing agent.

8. A composition according to claim 6, wherein said composition comprises: about 0.075% to 0.5% of said silicone emulsion.

9. A composition according to claim 6, wherein said composition comprises: about 0.1% to 1% sodium carboxymethyl cellulose; and about 0.0% to 0.1% methylparaben.

10. A composition according to claim 6, wherein said composition comprises: about 0.1% to 1.0% polyacrylamide.

11. A method for controlling insect pest, wherein said method comprises: applying to the habitat, food supply or breeding sites of said insect pests, an insecticidally-effective amount of an aqueous-based microemulsion composition; said composition containing about 1% to 20% of (±)-α-cyano-m-phenoxybenzyl (+)-2-[p-difluoromethoxy)-phenyl]-3-methylbutyrate; about 1.0% to 40% of the surfactant blend consiting of one or more components selected from the group consisting of calcium dodecylbenzene sulfonate, ethoxylated distyrylphenol ammonium sulfate with 5 moles of ethoxylation and ethoxylated tristyrylphenol with 17 moles of ethoxylation; about 0% to 12% thickening agents, antifoaming agents, antifreezing agents, antimicrobial preservatives or mixtures thereof; and water to total said composition to 100%.

12. A method according to claim 11, wherein said composition comprises: about 0% to 1.0% silicone emulsion antifoaming agent; about 0% to 10% alkyl or dialkyl glycol antifreezing agent; about 0.1% to 1.0% thickening agent; and about 0.0% to 0.2% methylparaben antimicrobial preservative.

13. A method according to claim 12, wherein said surfactant blend is 1.25% to 40%, on a weight to volume basis, of said composition.

14. A method according to claim 13, wherein said thickening agent includes cellulose derivatives, polyacylamides, polyvinyl acohols, polyvinyl pyrollidones, natural gums, and mixtures thereof.

15. A method according to claim 14, wherein said composition is applied to said habitat, food supply, or breeding site of said insect pests at concentrations of about 0.0025% to 1.5% of active ingredient.

16. A method for controlling insect pests utilizing ultra-low volume (ULV) application, said method comprising: applying to the habitat, food supply or breeding site of said insect pests, an insecticidal amount of an aqueous-based insecticidal microemulsion composition with finely divided discrete droplets having mass medium diameter size of about 17 to 150 microns, said composition containing, on a weight to volume basis, about 1% to 20% of ($\pm$)-$\alpha$-cyano-m-phenoxybenzyl (+)-2-[p-difluoromethoxy)-phenyl]-3-methylbutyrate; about 1.0% to 40% of the surfactant blend consisting of one or more components selected from the group consisting of calcium dodecylbenzene sulfonate, ethoxylated distyrylphenol ammonium sulfonate with 5 moles of ethoxylation and ethoxylated tristyrylphenol with 17 moles of ethoxylation; about 0% to 12% microemulsion adjuvants; and water to total said composition to 100%.

17. A method according to claim 16, wherein said microemulsion adjuvants comprise: about 0% to 1.0% silicone emulsion antifoaming agent; about 0% to 10% alkyl or dialkyl glycol antifreezing agent, about 0.1% to 1.0% thickening agent; and about 0.0% to 0.2% methylparaben antimicrobial preservative.

* * * * *